United States Patent
Schmuecking et al.

(10) Patent No.: US 12,175,668 B2
(45) Date of Patent: Dec. 24, 2024

(54) CARDIO AI SMART ASSISTANT FOR SEMANTIC IMAGE ANALYSIS OF MEDICAL IMAGING STUDIES

(71) Applicant: SIEMENS HEALTHINEERS AG, Forchheim (DE)

(72) Inventors: Ingo Schmuecking, Yardley, PA (US); Puneet Sharma, Princeton Junction, NJ (US); Desiree Komuves, Richardson, TX (US); Tiziano Passerini, Plainsboro, NJ (US); Paul Klein, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 357 days.

(21) Appl. No.: 17/659,208

(22) Filed: Apr. 14, 2022

(65) Prior Publication Data
US 2023/0334655 A1  Oct. 19, 2023

(51) Int. Cl.
*G06T 7/00* (2017.01)
*G16H 30/40* (2018.01)
*G16H 30/20* (2018.01)

(52) U.S. Cl.
CPC .......... *G06T 7/0012* (2013.01); *G16H 30/40* (2018.01); *G06T 2207/20081* (2013.01); *G06T 2207/30048* (2013.01); *G16H 30/20* (2018.01)

(58) Field of Classification Search
CPC ......... G06T 7/0012; G06T 2207/20081; G06T 2207/30048; G06T 2207/30101; G16H 30/40; G16H 30/20; G16H 50/20; G16H 50/70; G06V 10/764; G06V 10/803; G06V 10/82; G06V 10/96; G06V 2201/031
See application file for complete search history.

(56) References Cited

U.S. PATENT DOCUMENTS

2022/0031218 A1*  2/2022  Klein ................... A61B 5/308

OTHER PUBLICATIONS

Extended European Search Report (EESR) mailed Jun. 27, 2023 in corresponding European Patent Application 1 No. 23167898.8.
Mitchell et al., "Guidelines for Performing a Comprehensive Transthoracic Echocardiographic Examination in Adults: Recommendations from the American Society of Echocardiography", Journal of the American Society of Echocardiography, 2019, pp. 1-64.
Akkus et al., "Artificial Intelligence (AI)-Empowered Echocardiography Interpretation: A State-of-the-Art Review", Journal of Clinical Medicine, 2021, vol. 10, pp. 1-16.
Alsharqi et al., "Artificial intelligence and echocardiography", Bioscientifica, vol. 5, 2018, pp. R115-R125.

* cited by examiner

*Primary Examiner* — Ping Y Hsieh

(57) ABSTRACT

Systems and methods for determining a semantic image understanding of medical imaging studies are provided. A plurality of medical imaging studies associated with a plurality of medical imaging modalities is provided. Metadata associated with each of the plurality of medical imaging studies is generated by performing a plurality of semantic image analysis tasks using one or more machine learning based networks. The metadata associated with each of the plurality of medical imaging studies is output.

16 Claims, 5 Drawing Sheets

100

```
Receive a plurality of medical imaging studies
associated with a plurality of medical imaging
modalities
102
            │
            ▼
Generate metadata associated with each of
the plurality of medical imaging studies by
performing a plurality of semantic image
analysis tasks on images of the plurality of
medical imaging studies using one or more
machine learning based networks
104
            │
            ▼
Output the metadata associated with each of
the plurality of medical imaging studies
106
```

CARDIO AI SMART ASSISTANT FOR SEMANTIC IMAGE ANALYSIS OF MEDICAL IMAGING STUDIES

TECHNICAL FIELD

The present invention relates generally to a cardio AI (artificial intelligence) smart assistant, and in particular to a cardio AI smart assistant for semantic image analysis of medical imaging studies for automated image preparation in cardiovascular imaging workflows.

BACKGROUND

Medical imaging is important for the diagnosis and treatment of many cardiovascular diseases. For example, in a CVSL (cardiovascular service line), cardiovascular services and programs for diagnosing and treating cardiovascular diseases are provided using a large number of medical images acquired with different imaging modalities. In another example, imaging studies are performed by acquiring a large number of medical images to fully image the anatomy and function of the heart. In echocardiography, for example, this may include capturing different views and some of the views may be repeated multiple times with varying parameters until a clip with good image quality and coverage of the anatomy is obtained, which further increases the manual workload when reviewing the study. Traditionally, a clinician is given a short amount of time to manually evaluate medical images. However, much of that time is spent by the clinician searching for images, navigating the images, and arranging the images into a layout suitable for clinical review. Accordingly, such manual evaluation of medical images is time consuming, inefficient, and expensive.

A CVIS (cardiovascular imaging and information system) may be used to manage medical imaging and clinical data. The CVIS supports the creation of procedure reports and enables clinician review of images throughout a healthcare enterprise. However, many steps for reviewing medical images in a CVIS need to be manually performed. Further, at times, there is a need for clinicians to review prior studies stored in the CVIS. Review of such prior studies further adds to the workload of the clinician.

BRIEF SUMMARY OF THE INVENTION

In accordance with one or more embodiments, a cardio AI smart assistant is provided to generate metadata associated with medical imaging studies. Such metadata represents a semantic understanding of the medical imaging studies. The metadata of the medical imaging studies facilitates a more efficient review of the medical imaging studies by clinicians and increased diagnostic accuracy.

In one embodiment, systems and methods for determining a semantic image understanding of medical imaging studies are provided. A plurality of medical imaging studies associated with a plurality of medical imaging modalities is provided. Metadata associated with each of the plurality of medical imaging studies is generated by performing a plurality of semantic image analysis tasks using one or more machine learning based networks. The metadata associated with each of the plurality of medical imaging studies is output. The plurality of medical imaging studies may comprise a plurality of cardiovascular imaging studies In one embodiment, the metadata comprises one or more of a view classification of the plurality of medical imaging studies, identification of anatomical landmarks detected in the plurality of medical imaging studies, identification of anatomical structures detected in the plurality of medical imaging studies, a classification of a zoom level of the plurality of medical imaging studies, a classification of a cardiac phase shown in the plurality of medical imaging studies, a classification of a presence of a contrast enhancement in the plurality of medical imaging studies, an assessment of image quality of the plurality of medical imaging studies, or a score associated with the plurality of medical imaging studies.

In one embodiment, the one or more machine learning based networks comprises a single machine learning based network trained with multi-task learning for simultaneously performing the plurality of semantic image analysis tasks. In another embodiment, the one or more machine learning based networks comprises a plurality of machine learning based networks each for performing a respective one of the plurality of semantic image analysis tasks.

In one embodiment, a medical analysis task is performed based on the metadata using a second machine learning based network. In another embodiment, one or more predefined rules are applied on the metadata using a rule-based engine In one embodiment, feedback for completing an acquisition of a medical imaging study is transmitted. In another embodiment, the metadata is stored in a medical information system, such as, e.g., a CVIS (cardiovascular information system).

These and other advantages of the invention will be apparent to those of ordinary skill in the art by reference to the following detailed description and the accompanying drawings.

DETAILED DESCRIPTION

The present invention generally relates to methods and systems for semantic image analysis of medical imaging studies. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a cardio AI (artificial intelligence) smart assistant for facilitating automated image preparation of imaging studies stored in a CVIS (cardiovascular information system). The cardio AI smart assistant utilizes one or more machine learning based networks to perform a semantic image analysis to generate metadata associated with the imaging studies. The metadata represents a semantic image understanding of the imaging studies. Advantageously, the metadata facilitates a more efficient review of the medical imaging studies by clinicians and increased diagnostic accuracy. Further, the metadata may be utilized in downstream medical analysis tasks for a clinical workflow.

Figure 1:
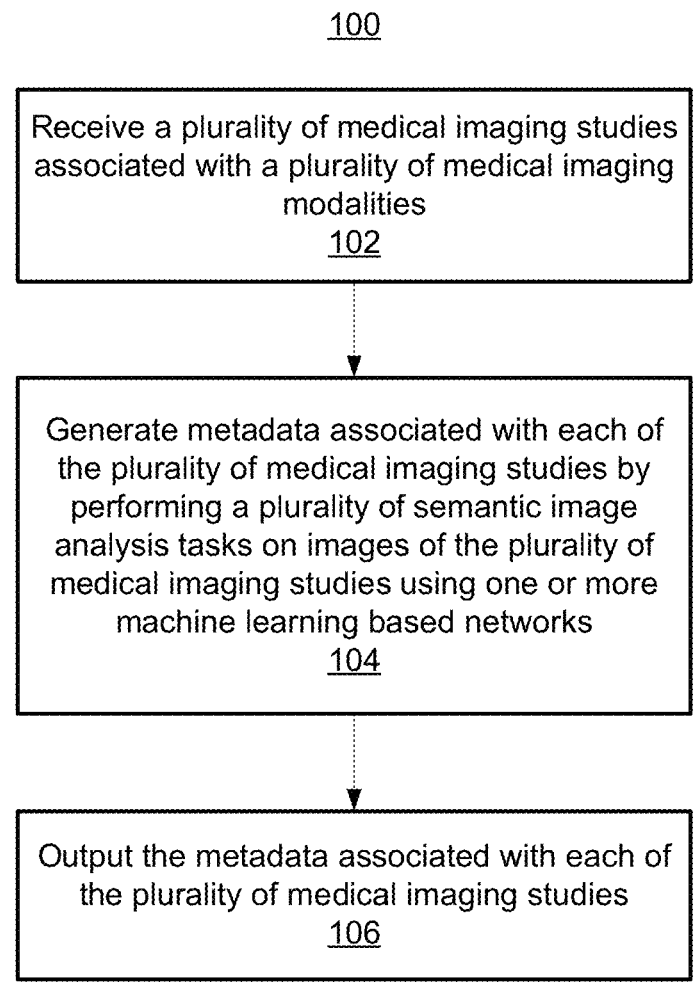
FIG. 1 shows a method for determining a semantic understanding of medical imaging studies, in accordance with one or more embodiments.
Figure 2:
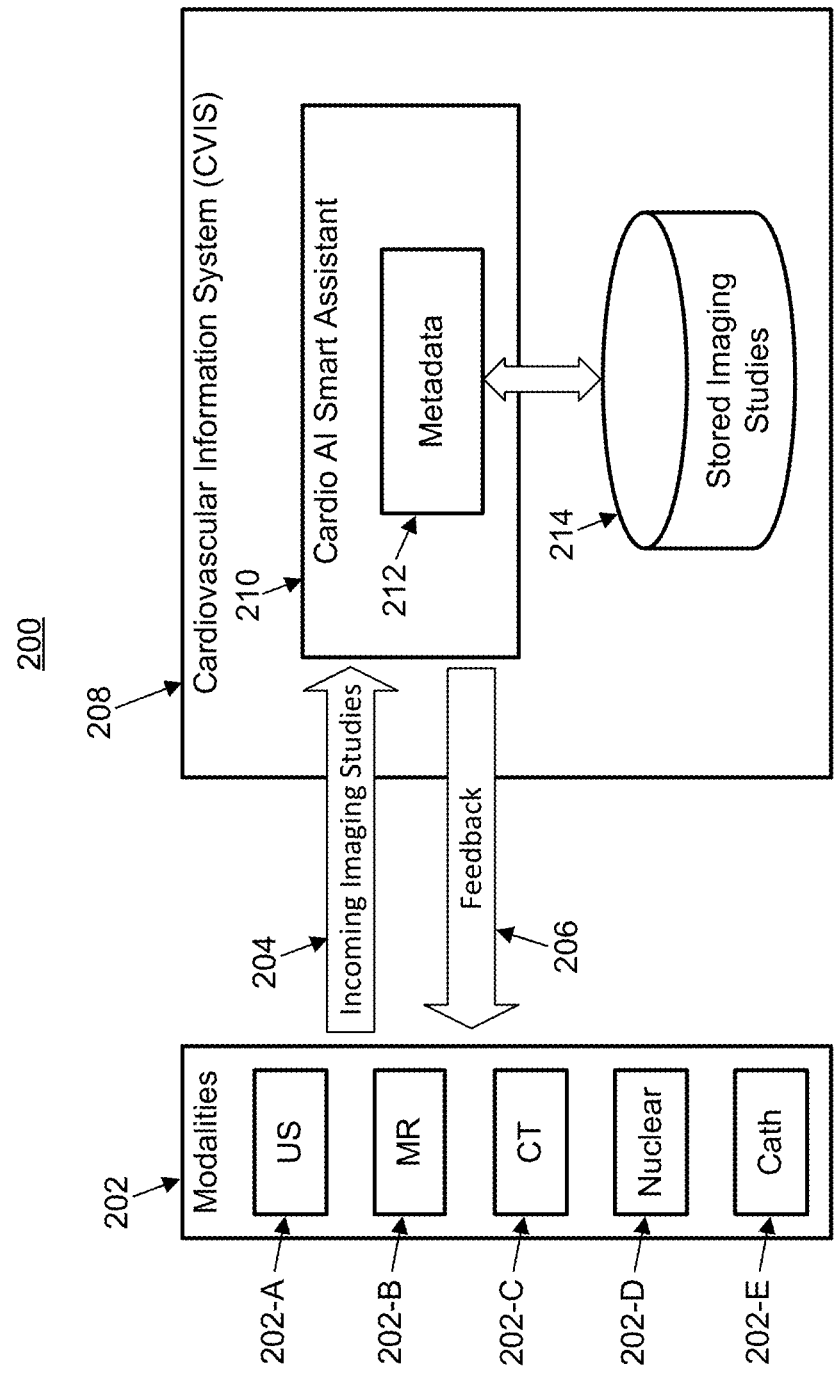
FIG. 2 shows a schematic diagram of a system for determining a semantic understanding of medical imaging studies, in accordance with one or more embodiments.

FIG. 1 shows a method 100 for determining a semantic understanding of medical imaging studies, in accordance with one or more embodiments. FIG. 2 shows a schematic diagram 200 of a system for determining a semantic understanding of medical imaging studies, in accordance with one or more embodiments. FIG. 1 and FIG. 2 will be described together. The steps of method 100 may be performed by one or more suitable computing devices, such as, e.g., computer 502 of FIG. 5. In one example, cardio AI smart assistant 210 of FIG. 2 may be implemented by a computing device such as, e.g., computer 502 of FIG. 5 and the steps of method 100 of FIG. 1 are performed by cardio AI smart assistant 210.

At step 102 of FIG. 1, a plurality of medical imaging studies associated with a plurality of medical imaging modalities is received. The medical imaging studies comprise medial images and other medical data of a patient. For example, the other medical data may include DICOM (digital imaging and communications in medicine) header data, measurements performed by clinicians on the images, information stored in a CVIS, procedure reports with findings and impressions, prior imaging studies used for comparison, etc. The DICOM header data may include, e.g., manufacturer and model, matrix size, number of frames, image compression, etc. The measurements performed by clinicians on the images may include, e.g., annotations and quantification results. The measurements may be performed during image acquisition (e.g., on cart) before images are transferred to the information system and/or off cart when the images are available in the information system. The measurements may be transferred to the information system in a DICOM SR (structured report) object. The information stored in the CVIS may include, e.g., an identification (e.g., by a user) of images as being "key images" within an imaging study. In one example, the medical imaging studies are cardiovascular imaging studies of the patient. However, the medical imaging studies may be any other suitable imaging studies of the patient.

In one example, as shown in FIG. 2, the medical imaging studies may be incoming imaging studies 204 of the patient or stored imaging studies 214 of the patient. Incoming imaging studies 204 comprise incoming imaging studies of the patient received by CVIS 208. Stored imaging studies 214 comprise previously acquired imaging studies of the patient stored in a storage or memory of CVIS 208 and received by retrieving the stored imaging studies from the storage or memory. While FIG. 2 is described with respect to CVIS 208, it should be understood that CVIS 208 may be any other suitable medical information system with database(s) for imaging and clinical data used for image reading, reporting and viewing, such as, e.g., a VNA (vendor neutral archive), an RIS (radiology information system), a PACS (picture archiving and communication systems), an EHR (electronic health records), etc.

The medical imaging modalities of the medical imaging studies may be any suitable modalities. For example, incoming imaging studies 204 and stored imaging studies 214 may be of modalities 202, such as, e.g., US (ultrasound) 202-A, MR (magnetic resonance) 202-B, CT (computed tomography) 202-C, nuclear 202-D, catheter images 202-E, or any other medical imaging modality or combinations of medical imaging modalities. The medical imaging studies may comprise 2D (two dimensional) images and/or 3D (three dimensional) volumes, and may each comprise a single medical image or a plurality of medical images. In one example, the medical imaging studies may comprise a 2D slice of a 3D volume.

At step 104 of FIG. 1, metadata associated with each of the plurality of medical imaging studies is generated by performing a plurality of semantic image analysis tasks on images of the plurality of medical imaging studies using one or more machine learning based networks. In one example, as shown in FIG. 2, the one or more machine learning based networks are implemented by cardio AI smart assistant 210 of CVIS 208 for generating metadata 212. The metadata may comprise any data extracted from the medical imaging studies. The metadata provides comprehensive and granular information of the imaging studies to thereby provide a semantic understanding of the medical imaging studies. While cardio AI smart assistant 210 is shown as being implemented as a part of CVIS 208, it should be understood that cardio AI smart assistant 210 may be implemented as a discrete component separate from CVIS 208.

It should be understood that the metadata generated at step 104 is not the same as the metadata stored in the DICOM header (e.g., matrix size, number of frames, manufacturer, etc.), but provides an additional set of information on image content. The metadata generated at step 104 may be stored in the information system and/or added as attributes to the imaging data. When added to the imaging data, the information could also be used in other systems.

The semantic image analysis tasks may comprise any task for extracting the metadata from the images of the medical imaging studies. In one or more embodiments, the semantic image analysis tasks comprises, e.g., a view classification task to classify a view of the medical imaging studies, an anatomical landmark detection task to detect anatomical landmarks shown in the medical imaging studies, an anatomical structure detection task to detect anatomical structures shown in the medical imaging studies, a zoom level classification task to classify the zoom level of the medical imaging studies, a cardiac phase classification task to classify a cardiac phase shown in the medica imaging studies, a contrast classification task to classify a presence of a contrast enhancement of the medical imaging studies, an image quality assessment task to generate an image quality assessment of the medical imaging studies, a scoring task to generate a score associated with the medical imaging studies, etc. The semantic image analysis task may comprise any other task for extracting the metadata from the medical imaging studies.

The view classification task may generate metadata comprising a classification of the medical imaging studies as showing, for example, a main view (e.g., a A4C (apical 4 chamber) view), a sub-type of views, etc. The anatomical landmarks detection task may generate metadata comprising an identification of anatomical landmarks, such as, e.g., mitral valve 1, mitral valve 2, true LV (left ventricle) apex, tricuspid valve 1, or any other anatomical landmark shown in the medical imaging studies. The anatomical structures detection task may generate metadata comprising an identification of anatomical structures, for example, LV, LA (left atrium), RV (right ventricle), RA (right atrium), mitral valve, or any other anatomical structure in the medical imaging studies. The zoom level classification task may generate metadata comprising a classification of the zoom level characterizing the field of view visible in the medical imaging studies. The cardiac phase classification task may generate metadata comprising a classification of the cardiac phase shown in the medical imaging studies as being, for example, an end diastole or an end systole. The contrast classification task may generate metadata comprising a classification of the presence of contrast enhancement in the medical imaging studies. The image quality assessment task may generate metadata comprising an assessment of image quality, such as, e.g., noise level, image artifacts, image quality for each relevant cardiac structure (e.g., LV or RV), etc. for the medical imaging studies. The scoring task may generate metadata comprising a score for a particular use case such as, e.g., a score based on image quality at specific phases of the cardiac cycle as well as anatomical structures shown in the medical imaging studies.

The one or more machine learning based networks may be implemented according to any suitable machine learning based architecture for performing the semantic image analysis tasks, such as, e.g., a DNN (deep neural network), a CNN (convolutional neural network), a DI2IN (deep image-to-image network), etc. In one embodiment, the one or more machine learning based networks comprises a single machine learning based network trained using multi-task learning to simultaneously perform each of the plurality of semantic image analysis tasks. The machine learning based network comprises 1) an encoder for encoding each of the medical imaging studies into shared features (i.e., latent features or a latent representation) and 2) a plurality of decoders each for decoding the shared features to perform a respective one of the semantic image analysis tasks. By utilizing a single machine learning based network, results of each of the semantic image analysis tasks are ensured to be consistent. In another embodiment, the one or more machine learning based networks comprises a plurality of machine learning based networks each for performing a respective one of the semantic image analysis tasks. The one or more machine learning based networks are trained to perform the semantic image analysis tasks during a prior offline or training stage based on annotated training data. Once trained, the trained machine learning based model is applied (e.g., at step 104 of FIG. 1) to perform the semantic image analysis tasks during an online or testing stage.

At step 106 of FIG. 1, the metadata associated with each of the plurality of medical imaging studies is output. For example, the metadata associated with each of the plurality of medical imaging studies can be output by displaying the metadata on a display device of a computer system, storing the metadata on a memory or storage of a computer system, or by transmitting the metadata to a remote computer system.

In one embodiment, the metadata is output and stored in a structured format (e.g., as a table, a spreadsheet, a CSV (comma-separated values) file, etc.) with a predefined set of fields. The structured metadata is output to downstream system (e.g., a second machine learning based network, such as, e.g., a deep learning network) to perform a medical analysis task. In one embodiment, the second machine learning based network may associate the values of the structured metadata to various measures of interest for a clinical application. For example, a good-quality A4C view with all tricuspid valve landmarks visible can be used for RV function assessment. The second machine learning based network can be trained with supervision as a classifier to discriminate between a finite set of discrete options.

In one embodiment, the metadata is output to a rule-based engine and the rule-based engine applies one or more predefined rules on the metadata to perform various tasks, such as, e.g., displaying a message to the user, reordering the order of presentation of the medical imaging studies to the user, etc.

In one embodiment, the metadata may be used for image review and reporting or for image viewing (e.g., call-up from EHR, mobile access, etc.). In one embodiment, cardio AI smart assistant 210 automatically processes incoming imaging studies 204 received by CVIS 208 to generate the metadata. The metadata may be transmitted to CVIS 208 for storing the metadata in CVIS 208. In another embodiment, cardio AI smart assistant automatically processes stored imaging studies 214, which are associated with CVIS 208, to generate the metadata for storing in CVIS 208. Cardio AI smart assistant 210 may be implemented on premises (e.g., of a clinic) and/or may be implemented in the cloud.

In one embodiment, the images of the medical imaging studies processed by cardio AI smart assistant 210 may be original DICOM images and/or compressed images. The processing of compressed images may be performed in situations with, e.g., low bandwidth.

In one embodiment, cardio AI smart assistant 210 may determine the completeness of image acquisition protocols (e.g., standardized protocols for complete transthoracic echocardiography exams with defined views to be imaged).

In one embodiment, cardio AI smart assistant 210 analyzes images and clips from the medical imaging studies that are in progress of being acquired and transmits feedback 206 for completing the acquisition. For example, feedback 206 may comprise exam completion information transmitted to the acquisition device.

In one embodiment, cardio AI smart assistant 210 determines images of the medical imaging studies that are most suitable for a specific use case (e.g., clinical measurement) among multiple images of the same view in a study (e.g., multiple images with A4C views).

In one embodiment, the metadata generated by cardio AI smart assistant 210 enables execution of automatic tasks (e.g., automatic measurement protocols) in the medical imaging studies using the most suitable images prior to the medical imaging studies being opened by a user. The automatic measurement protocols may be tailored to the clinical condition for which the exam was performed (e.g., aortic stenosis).

In one embodiment, the cardio AI smart assistant 210 may propose the most suitable image in a medical imaging study based on the measurement tool selected by the user. The cardio AI smart assistant 210 may then automatically navigate to the image and frame.

In one embodiment, the cardio AI smart assistant 210 matches images from a current medical imaging study with the most suitable comparable images from prior stored imaging studies 214 for the purpose of temporal comparison. The images can be automatically displayed side-by-side without manual user interaction.

In one embodiment, the metadata enables semantic search across current incoming imaging studies 204 and prior stored imaging studies 214. For example, the semantic search may find all images with a A4C view of a patient. The semantic search may include one or multiple semantic criteria.

In one embodiment, the cardio AI smart assistant 210 determines a content-driven display (e.g., layout) of images for specific use cases, which may be based on the clinical condition (e.g., aortic stenosis), the reading environment (e.g., diagnostic workstation, laptop, or mobile device), or the care setting (e.g., clinical conference, review by referring clinician), and may include images from one or more imaging studies. For example, multiple imaging studies may comprise current and prior imaging studies from the same modality (e.g., echo) or different modalities (e.g., echo and MR).

In one embodiment, the cardio AI smart assistant 210 may be applied to process adult cardiovascular imaging studies, process pediatric cardiovascular imaging studies, process entire imaging studies from multiple cardiovascular imaging modalities, process images acquired with image acquisition devices from different manufacturers, support processing of original quality and compressed images, perform various semantic image analysis tasks such as, e.g., view classification, cardiac phase detection, image quality assessment, and to generate reasoning to derive scores based on multiple individual parameters. The "original quality" images refer to the images as they were received from the modality. The "compressed" images may be the original quality images compressed on the modality (e.g., lossless or lossy) before they sent to the medical information system. The medical information system may apply additional compression to reduce size for storage or to handle images more efficiently in low-bandwidth situations. The embodiments described herein are able to process images compressed with any level of compression that may be used in the system.

Advantageously, embodiments described herein provide for a more efficient review of medical imaging studies and for increased diagnostic accuracy. Further, embodiments described herein enhance consistency across users in a clinical department or across a hospital. In additional, embodiments described herein increase efficiencies in operating large scale CVIS implementations as, for example, adding new medical imaging studies in a multi-vendor environment is less labor intensive.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 3:
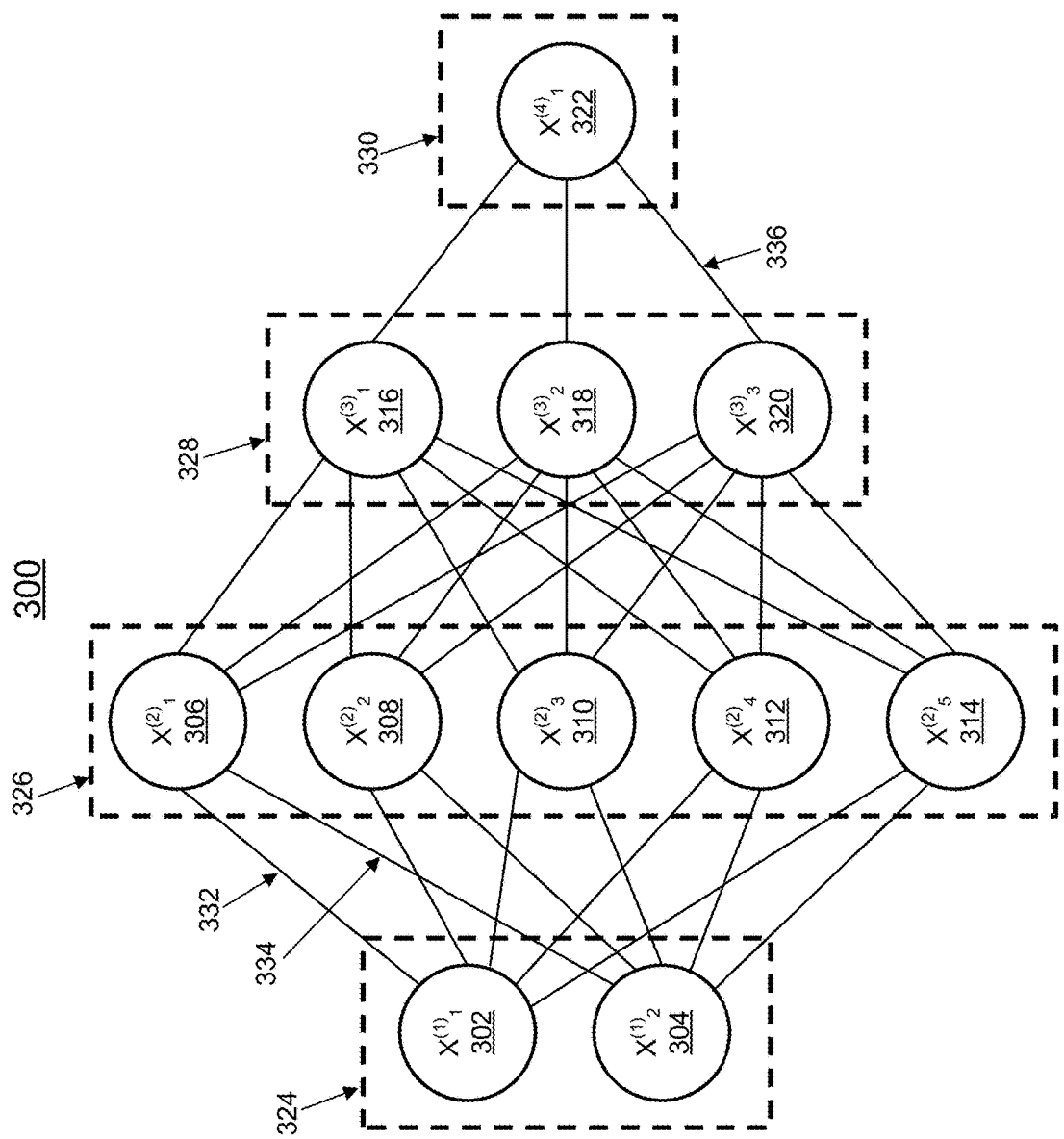
FIG. 3 shows an exemplary artificial neural network that may be used to implement one or more embodiments.

FIG. 3 shows an embodiment of an artificial neural network 300, in accordance with one or more embodiments. Alternative terms for "artificial neural network" are "neural network", "artificial neural net" or "neural net". Machine learning networks described herein, such as, e.g., the one or more machine learning based networks utilized at step 104 of FIG. 1, may be implemented using artificial neural network 300.

The artificial neural network 300 comprises nodes 302-322 and edges 332, 334, . . . , 336, wherein each edge 332, 334, . . . , 336 is a directed connection from a first node 302-322 to a second node 302-322. In general, the first node 302-322 and the second node 302-322 are different nodes 302-322, it is also possible that the first node 302-322 and the second node 302-322 are identical. For example, in FIG. 3, the edge 332 is a directed connection from the node 302 to the node 306, and the edge 334 is a directed connection from the node 304 to the node 306. An edge 332, 334, . . . , 336 from a first node 302-322 to a second node 302-322 is also denoted as "ingoing edge" for the second node 302-322 and as "outgoing edge" for the first node 302-322.

In this embodiment, the nodes 302-322 of the artificial neural network 300 can be arranged in layers 324-330, wherein the layers can comprise an intrinsic order introduced by the edges 332, 334, . . . , 336 between the nodes 302-322. In particular, edges 332, 334, . . . , 336 can exist only between neighboring layers of nodes. In the embodiment shown in FIG. 3, there is an input layer 324 comprising only nodes 302 and 304 without an incoming edge, an output layer 330 comprising only node 322 without outgoing edges, and hidden layers 326, 328 in-between the input layer 324 and the output layer 330. In general, the number of hidden layers 326, 328 can be chosen arbitrarily. The number of nodes 302 and 304 within the input layer 324 usually relates to the number of input values of the neural network 300, and the number of nodes 322 within the output layer 330 usually relates to the number of output values of the neural network 300.

In particular, a (real) number can be assigned as a value to every node 302-322 of the neural network 300. Here, $x^{(n)}_i$ denotes the value of the i-th node 302-322 of the n-th layer 324-330. The values of the nodes 302-322 of the input layer 324 are equivalent to the input values of the neural network 300, the value of the node 322 of the output layer 330 is equivalent to the output value of the neural network 300. Furthermore, each edge 332, 334, . . . , 336 can comprise a weight being a real number, in particular, the weight is a real number within the interval [−1, 1] or within the interval [0, 1]. Here, $w^{(m,n)}_{i,j}$ denotes the weight of the edge between the i-th node 302-322 of the m-th layer 324-330 and the j-th node 302-322 of the n-th layer 324-330. Furthermore, the abbreviation $w^{(n)}_{i,j}$ is defined for the weight $w^{(n,n+1)}_{i,j}$.

In particular, to calculate the output values of the neural network 300, the input values are propagated through the neural network. In particular, the values of the nodes 302-322 of the (n+1)-th layer 324-330 can be calculated based on the values of the nodes 302-322 of the n-th layer 324-330 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 324 are given by the input of the neural network 300, wherein values of the first hidden layer 326 can be calculated based on the values of the input layer 324 of the neural network, wherein values of the second hidden layer 328 can be calculated based in the values of the first hidden layer 326, etc.

In order to set the values $w^{(m,n)}_{i,j}$ for the edges, the neural network 300 has to be trained using training data. In particular, training data comprises training input data and training output data (denoted as ti). For a training step, the neural network 300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 300 (backpropagation algorithm). In particular, the weights are changed according to $$w'^{(m,n)}_{i,j} = w^{(n)}_{i,j} - \gamma \cdot \delta_j^{(n)} \cdot x_j^{(n)}$$

wherein $\gamma$ is a learning rate, and the numbers $\delta^{(n)}_j$ can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 330, wherein f' is the first derivative of the activation function, and $y^{(n+1)}_j$ is the comparison training value for the j-th node of the output layer 330.

Figure 4:
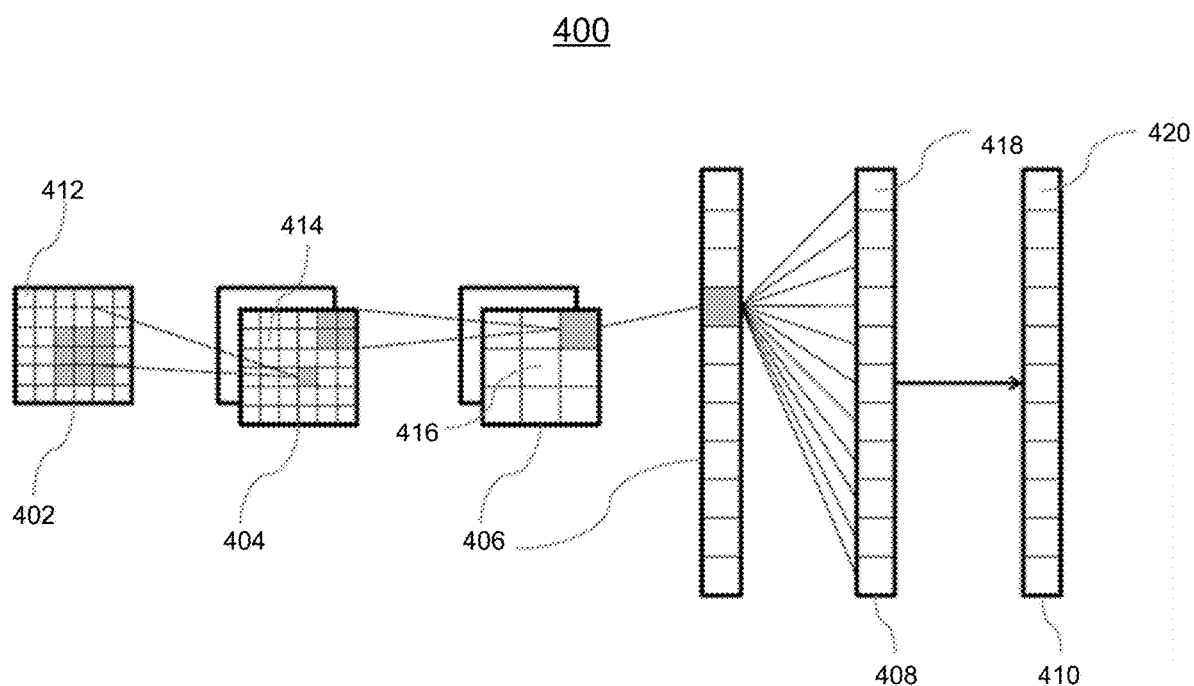
FIG. 4 shows a convolutional neural network that may be used to implement one or more embodiments.

FIG. 4 shows a convolutional neural network 400, in accordance with one or more embodiments. Machine learning networks described herein, such as, e.g., the one or more machine learning based networks utilized at step 104 of FIG. 1, may be implemented using convolutional neural network 400.

In the embodiment shown in FIG. 4, the convolutional neural network comprises 400 an input layer 402, a convolutional layer 404, a pooling layer 406, a fully connected layer 408, and an output layer 410. Alternatively, the convolutional neural network 400 can comprise several convolutional layers 404, several pooling layers 406, and several fully connected layers 408, as well as other types of layers. The order of the layers can be chosen arbitrarily, usually fully connected layers 408 are used as the last layers before the output layer 410.

In particular, within a convolutional neural network 400, the nodes 412-420 of one layer 402-410 can be considered to be arranged as a d-dimensional matrix or as a d-dimensional image. In particular, in the two-dimensional case the value of the node 412-420 indexed with i and j in the n-th layer 402-410 can be denoted as $x^{(n)}_{[i,j]}$. However, the arrangement of the nodes 412-420 of one layer 402-410 does not have an effect on the calculations executed within the convolutional neural network 400 as such, since these are given solely by the structure and the weights of the edges.

In particular, a convolutional layer 404 is characterized by the structure and the weights of the incoming edges forming a convolution operation based on a certain number of kernels. In particular, the structure and the weights of the incoming edges are chosen such that the values $x^{(n)}_k$ of the nodes 414 of the convolutional layer 404 are calculated as a convolution $x^{(n)}_k = K_k * x^{(n-1)}$ based on the values $x^{(n-1)}$ of the nodes 412 of the preceding layer 402, where the convolution * is defined in the two-dimensional case as $$x_k^{(n)}[i, j] = (K_k * x^{(n-1)})[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 412-418 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 412-420 in the respective layer 402-410. In particular, for a convolutional layer 404, the number of nodes 414 in the convolutional layer is equivalent to the number of nodes 412 in the preceding layer 402 multiplied with the number of kernels.

If the nodes 412 of the preceding layer 402 are arranged as a d-dimensional matrix, using a plurality of kernels can be interpreted as adding a further dimension (denoted as "depth" dimension), so that the nodes 414 of the convolutional layer 404 are arranged as a (d+1)-dimensional matrix. If the nodes 412 of the preceding layer 402 are already arranged as a (d+1)-dimensional matrix comprising a depth dimension, using a plurality of kernels can be interpreted as expanding along the depth dimension, so that the nodes 414 of the convolutional layer 404 are arranged also as a (d+1)-dimensional matrix, wherein the size of the (d+1)- dimensional matrix with respect to the depth dimension is by a factor of the number of kernels larger than in the preceding layer 402.

The advantage of using convolutional layers 404 is that spatially local correlation of the input data can exploited by enforcing a local connectivity pattern between nodes of adjacent layers, in particular by each node being connected to only a small region of the nodes of the preceding layer.

In embodiment shown in FIG. 4, the input layer 402 comprises 36 nodes 412, arranged as a two-dimensional 6×6 matrix. The convolutional layer 404 comprises 72 nodes 414, arranged as two two-dimensional 6×6 matrices, each of the two matrices being the result of a convolution of the values of the input layer with a kernel. Equivalently, the nodes 414 of the convolutional layer 404 can be interpreted as arranges as a three-dimensional 6×6×2 matrix, wherein the last dimension is the depth dimension.

A pooling layer 406 can be characterized by the structure and the weights of the incoming edges and the activation function of its nodes 416 forming a pooling operation based on a non-linear pooling function f. For example, in the two dimensional case the values $x^{(n)}$ of the nodes 416 of the pooling layer 406 can be calculated based on the values $x^{(n-1)}$ of the nodes 414 of the preceding layer 404 as $$x^{(n)}{}_{[i,j]} = f(x^{(n-1)}[id_1, jd_2], \ldots, x^{(n-1)}[id_1+d_1-1, jd_2+d_2-1])$$

In other words, by using a pooling layer 406, the number of nodes 414, 416 can be reduced, by replacing a number $d_1 \cdot d_2$ of neighboring nodes 414 in the preceding layer 404 with a single node 416 being calculated as a function of the values of said number of neighboring nodes in the pooling layer. In particular, the pooling function f can be the max-function, the average or the L2-Norm. In particular, for a pooling layer 406 the weights of the incoming edges are fixed and are not modified by training.

The advantage of using a pooling layer 406 is that the number of nodes 414, 416 and the number of parameters is reduced. This leads to the amount of computation in the network being reduced and to a control of overfitting.

In the embodiment shown in FIG. 4, the pooling layer 406 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 408 can be characterized by the fact that a majority, in particular, all edges between nodes 416 of the previous layer 406 and the nodes 418 of the fully-connected layer 408 are present, and wherein the weight of each of the edges can be adjusted individually.

In this embodiment, the nodes 416 of the preceding layer 406 of the fully-connected layer 408 are displayed both as two-dimensional matrices, and additionally as non-related nodes (indicated as a line of nodes, wherein the number of nodes was reduced for a better presentability). In this embodiment, the number of nodes 418 in the fully connected layer 408 is equal to the number of nodes 416 in the preceding layer 406. Alternatively, the number of nodes 416, 418 can differ.

Furthermore, in this embodiment, the values of the nodes 420 of the output layer 410 are determined by applying the Softmax function onto the values of the nodes 418 of the preceding layer 408. By applying the Softmax function, the sum the values of all nodes 420 of the output layer 410 is 1, and all values of all nodes 420 of the output layer are real numbers between 0 and 1.

A convolutional neural network 400 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 400 can be trained based on the backpropagation algorithm. For preventing overfitting, methods of regularization can be used, e.g. dropout of nodes 412-420, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
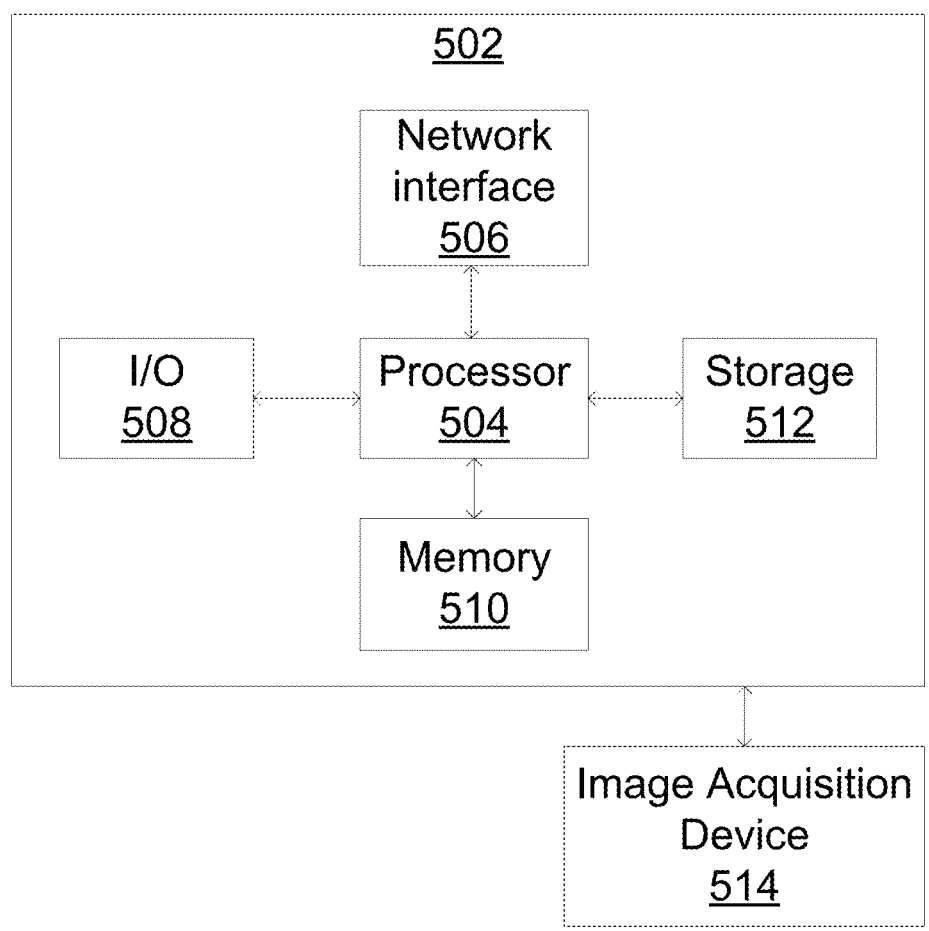
FIG. 5 shows a high-level block diagram of a computer that may be used to implement one or more embodiments.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIG. 1 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIG. 1. Accordingly, by executing the computer program instructions, the processor 504 executes the method and workflow steps or functions of FIG. 1. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

Any or all of the systems and apparatus discussed herein may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising
receiving a plurality of medical imaging studies associated with a plurality of medical imaging modalities;
generating metadata associated with each of the plurality of medical imaging studies by simultaneously performing a plurality of semantic image analysis tasks on images of the plurality of medical imaging studies using a single machine learning based network trained with multi-task learning, the machine learning based network comprising an encoder for encoding each of the plurality of medical imaging studies into shared features and a plurality of decoders each for decoding the shared features to perform a respective one of the plurality of semantic image analysis tasks; and
outputting the metadata associated with each of the plurality of medical imaging studies.

2. The computer-implemented method of claim 1, wherein the metadata comprises one or more of a view classification of the plurality of medical imaging studies, identification of anatomical landmarks detected in the plurality of medical imaging studies, identification of anatomical structures detected in the plurality of medical imaging studies, a classification of a zoom level of the plurality of medical imaging studies, a classification of a cardiac phase shown in the plurality of medical imaging studies, a classification of a presence of a contrast enhancement in the plurality of medical imaging studies, an assessment of image quality of the plurality of medical imaging studies, or a score associated with the plurality of medical imaging studies.

3. The computer-implemented method of claim 1, further comprising:
performing a medical analysis task based on the metadata using a second machine learning based network.

4. The computer-implemented method of claim 1, further comprising:
applying one or more predefined rules on the metadata using a rule-based engine.

5. The computer-implemented method of claim 1, further comprising:
transmitting feedback for completing an acquisition of a medical imaging study.

6. The computer-implemented method of claim 1, further comprising:
storing the metadata in a medical information system.

7. The computer-implemented method of claim 1, wherein the plurality of medical imaging studies comprises a plurality of cardiovascular imaging studies.

8. An apparatus comprising:
means for receiving a plurality of medical imaging studies associated with a plurality of medical imaging modalities;
means for generating metadata associated with each of the plurality of medical imaging studies by simultaneously performing a plurality of semantic image analysis tasks on images of the plurality of medical imaging studies using a single machine learning based network trained with multi-task learning, the machine learning based network comprising an encoder for encoding each of the plurality of medical imaging studies into shared features and a plurality of decoders each for decoding the shared features to perform a respective one of the plurality of semantic image analysis tasks; and
means for outputting the metadata associated with each of the plurality of medical imaging studies.

9. The apparatus of claim 8, wherein the metadata comprises one or more of a view classification of the plurality of medical imaging studies, identification of anatomical landmarks detected in the plurality of medical imaging studies, identification of anatomical structures detected in the plurality of medical imaging studies, a classification of a zoom level of the plurality of medical imaging studies, a classification of a cardiac phase shown in the plurality of medical imaging studies, a classification of a presence of a contrast enhancement in the plurality of medical imaging studies, an assessment of image quality of the plurality of medical imaging studies, or a score associated with the plurality of medical imaging studies.

10. The apparatus of claim 8, further comprising:
means for performing a medical analysis task based on the metadata using a second machine learning based network.

11. A non-transitory computer readable medium storing computer program instructions, the computer program instructions when executed by a processor cause the processor to perform operations comprising:
receiving a plurality of medical imaging studies associated with a plurality of medical imaging modalities;
generating metadata associated with each of the plurality of medical imaging studies by simultaneously performing a plurality of semantic image analysis tasks on images of the plurality of medical imaging studies using a single machine learning based network trained with multi-task learning, the machine learning based network comprising an encoder for encoding each of the plurality of medical imaging studies into shared features and a plurality of decoders each for decoding the shared features to perform a respective one of the plurality of semantic image analysis tasks; and
outputting the metadata associated with each of the plurality of medical imaging studies.

12. The non-transitory computer readable medium of claim 11, wherein the metadata comprises one or more of a view classification of the plurality of medical imaging studies, identification of anatomical landmarks detected in the plurality of medical imaging studies, identification of anatomical structures detected in the plurality of medical imaging studies, a classification of a zoom level of the plurality of medical imaging studies, a classification of a cardiac phase shown in the plurality of medical imaging studies, a classification of a presence of a contrast enhancement in the plurality of medical imaging studies, an assessment of image quality of the plurality of medical imaging studies, or a score associated with the plurality of medical imaging studies.

13. The non-transitory computer readable medium of claim 11, the operations further comprising:
applying one or more predefined rules on the metadata using a rule-based engine.

14. The non-transitory computer readable medium of claim 11, the operations further comprising:
transmitting feedback for completing an acquisition of a medical imaging study.

15. The non-transitory computer readable medium of claim 11, the operations further comprising:
storing the metadata in a medical information system.

16. The non-transitory computer readable medium of claim 11, wherein the plurality of medical imaging studies comprises a plurality of cardiovascular imaging studies.

\* \* \* \* \*